United States Patent [19]
Bley et al.

[11] Patent Number: 5,762,630
[45] Date of Patent: Jun. 9, 1998

[54] THERMALLY SOFTENING STYLET

[75] Inventors: Robert Bley, Menlo Park; Glenn Kubacki, Cupertino, both of Calif.

[73] Assignee: Johnson & Johnson Medical, Inc., Arlington, Tex.

[21] Appl. No.: 772,401

[22] Filed: Dec. 23, 1996

[51] Int. Cl.$^6$ .................................................. A61M 5/178
[52] U.S. Cl. ........................ 604/164; 604/264; 604/272; 604/280; 128/772
[58] Field of Search ........................ 604/110, 158, 604/164, 264–5, 280, 272; 128/768, 772

[56] References Cited

U.S. PATENT DOCUMENTS

| | | | |
|---|---|---|---|
| 4,610,671 | 9/1986 | Luther | 604/168 |
| 4,710,181 | 12/1987 | Fuqua | 604/280 |
| 4,816,021 | 3/1989 | Johnson | 604/110 |
| 4,838,877 | 6/1989 | Massau | 604/272 |
| 4,840,622 | 6/1989 | Hardy | 604/264 |
| 4,846,812 | 7/1989 | Walker et al. | 604/264 |
| 4,883,699 | 11/1989 | Aniuk et al. | 428/36.9 |
| 4,911,691 | 3/1990 | Aniuk et al. | 604/164 |
| 4,955,863 | 9/1990 | Walker et al. | 604/165 |
| 4,976,704 | 12/1990 | McLees | 604/265 |
| 5,102,401 | 4/1992 | Lambert et al. | 604/264 |
| 5,112,312 | 5/1992 | Luther | 604/177 |
| 5,120,317 | 6/1992 | Luther | 604/158 |
| 5,441,489 | 8/1995 | Utsumi et al. | 604/280 |
| 5,458,614 | 10/1995 | Humphrey | 604/239 |
| 5,484,565 | 1/1996 | Larsen et al. | 264/230 |
| 5,634,913 | 6/1997 | Stinger | 604/272 |

OTHER PUBLICATIONS

Shirai et al., "Development of Polymeric Shape Memory Material," *Nagoya Research & Development Center*, MTB 184, Dec. 1988, pp. 1–5.

Memry Technologies, Inc., "Shape Memory Polymer," (11 pages).

Mitsubishi Heavy Industries, Ltd., "Processing Instructions for Mitsubishi Shape Memory Polymer," No. 1, Rev. 2.2, Apr. 1992, pp. 1–23.

*Primary Examiner*—Sam Rimell
*Assistant Examiner*—Robert V. Racunas
*Attorney, Agent, or Firm*—Blakely, Sokoloff, Taylor & Zafman

[57] ABSTRACT

The present invention describes a stylet that softens dramatically upon insertion into a living body with a temperature of about 37° C. The stylet has a distal end and a proximal end. Upon insertion of the distal end into a living body, the distal end softens from a stiffness of about 78 Durometer Shore D units to 25 Durometer Shore D units in a preferred embodiment. Moreover, the proximal end of the stylet, which is not inserted into the living body, retains its stiffness to aid a physician or a nurse in inserting and placing the catheter and stylet assembly.

17 Claims, 3 Drawing Sheets

THERMALLY SOFTENING STYLET

BACKGROUND OF THE INVENTION

1. Field of the Invention

The present invention relates generally to medical devices. More specifically, the present invention pertains to a stylet that is disposed within a medical device, such as a catheter.

2. Description of Related Art

Catheters are used to extract and/or infuse a fluid into a living subject, such as a human patient. It is well-known that it is desirable for a catheter to have a certain amount of stiffness to aid insertion. Catheters are, however, often made of a soft, pliable, bio-compatible material, such as polyurethane. As a result, a metal stylet is often placed inside the catheter to provide stiffness. This stiffness is required to quickly and easily insert the catheter into a patient. Thus, the stylet is one method of providing stiffness to aid insertion of the catheter.

But it is also desirable for a catheter to have the ability to soften and/or expand once inserted to reduce patient trauma and to increase patient comfort. This is especially important for peripherally inserted central catheters (PICCs) that remain in a patient for long periods of time, for example, two weeks to a month. Several solutions are well-known in the prior art. One answer is to form the catheter or part of the catheter from a hydrophilic polymeric component that softens and/or swells when the catheter is substantially hydrated inside the patient. This softening process can require anywhere from an hour to several hours and in some cases, a few days to be complete. Consequently, the catheter did not soften and/or expand until after the catheter had been completely inserted and placed in its final indwelling point. See, e.g., U.S. Pat. No. 4,911,691 by Anuik et al. for an "Assembly For Administering IV Solution", which is assigned to Menlo Care. Thus, the initial insertion and placement of the catheter occurred without the benefit of a softer catheter.

Another prior art solution is to form the catheter or part of the catheter out of a thermally-softening polymeric material. In some cases, the thermally-softening material also had a shape memory component, so upon exposure to a predetermined heightened temperature, the catheter softened and/or expanded and/or returned to a predetermined shape. Typically, the thermally-softening polymeric material used had a glass transition temperature ($T_g$) near the patient's body temperature. Upon exposure to its $T_g$, the thermally-softening material typically softens at least 25 Durometer Shore D points. This softening process usually lasts about a few seconds.

All of the prior art solutions focused on having a softer catheter inside the patient, especially for those situations when the catheter remains in a patient for several weeks. Unfortunately, the catheter's softness during insertion is limited by a metal stylet, which is typically placed within the catheter to aid insertion and placement of the catheter. In particular, the metal stylet is necessary to guide and insert the pliable catheter, such as a longer-line catheter (e.g., a PICC) that must travel from six-to-twenty inches inside the patient. Thus, regardless of the softness of the catheter, the patient could still be affected by the metal stylet during insertion and placement of the catheter and stylet assembly. Thus, none of the prior art solutions considered making a softer stylet to achieve greater patient comfort during the insertion and placement of the stylet and catheter assembly. This is because a stiff stylet has been believed to be essential to insert and to place the soft pliable catheter. Consequently, during the tortuous path of twists and turns to reach the catheter's final indwelling point, the metal stylet may traumatize or damage the patient's blood vessel, or perforate the catheter. Thus, a softer stylet that increases patient comfort during the insertion and placement of the stylet and catheter assembly is desirable. It is also desirable that the softer stylet still be stiff enough outside the patient to facilitate inserting and placing the catheter into the patient.

SUMMARY

The present invention describes a stylet to aid insertion and/or placement of a catheter by quickly softening when the stylet is placed or inserted inside a living subject. In one embodiment, the stylet is an elongated member having a proximal end and a distal end. Upon inserting the distal end of the stylet into a living subject, the distal end quickly softens in response to the higher temperature (or warmth) of the living body. In contrast, the proximal end of the stylet, which is outside the living subject, does not soften but maintains its stiffness. Since the stylet is often placed within a catheter, for example a PICC, that must travel from six to twenty inches before reaching its final indwelling point, a softened stylet should help minimize vessel trauma and increase patient comfort. In addition, a softer stylet decreases the possibility of patient trauma during the insertion and placement of the stylet and catheter assembly. In a preferred embodiment, the stylet can be made of a shape memory polymer MM-3510 that is produced by Mitsubishi Heavy Industries, Ltd. and, which has a glass transition temperature ($T_g$) of 35° C. At 35° C., shape memory polymer MM-3510 decreases in stiffness from approximately 78 Durometer Shore D units to 25 Durometer Shore D units.

BRIEF DESCRIPTION OF THE DRAWINGS

The present invention is illustrated by way of example and not by way of limitation in the figures of the accompanying drawings in which like references indicate similar elements. In addition, for the sake of clarity, certain elements in a figure may appear larger and are not drawn to scale.

DETAILED DESCRIPTION

Figure 1A:
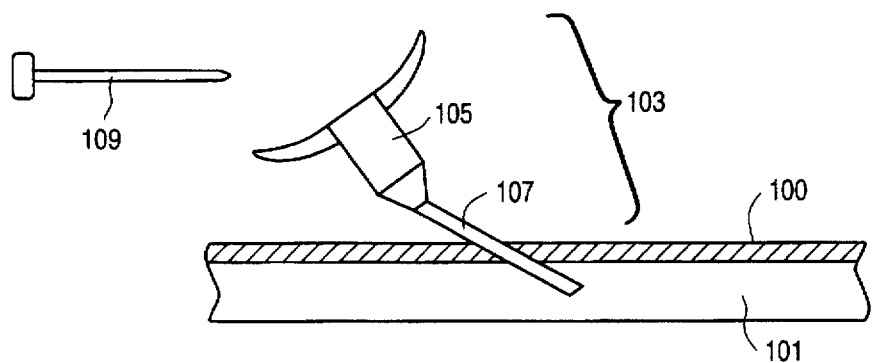
FIGS. 1A-1E illustrate one embodiment of the present invention.

A thermally-softening stylet for reducing vessel trauma and increasing patient comfort as the stylet and catheter assembly are inserted and placed in a patient is described. In the following description, numerous specific details are set forth in order to provide a thorough understanding of the present invention. It will be apparent, however, to one skilled in the art that the present invention may be practiced without these specific details. In other instances, well-known structures may not be shown in order to avoid unnecessarily obscuring the present invention. In other cases, specific examples are described and shown in order to thoroughly describe the invention. It will be appreciated that these specific examples are for the purpose of explanation and that alternative embodiments will be understood by those in the art.

The present invention provides several advantages over the prior art. The stylet of the present invention softens dramatically upon insertion into a living subject, such as a human patient. Since a catheter can be very thin, the patient can feel the catheter and stylet assembly as it is inserted and manipulated through the patient's blood vessels. In addition, although not perceptible to the patient, a certain amount of vessel trauma may occur. Unlike some prior art materials, which only considered softening the catheter, the present invention also considers the impact of the stylet's stiffness on the patient. Unlike prior art catheter materials that softened in an hour, a few hours or even days, the distal (i.e., inserted) end of the stylet softens almost instantaneously upon insertion into the patient. Thus, the patient receives the benefit of a softer stylet during the insertion and placement of the stylet and catheter assembly, which together form a vascular access device.

Moreover, because the stylet softens dramatically, the stylet and catheter assembly is less likely to irritate and perhaps perforate the patient's blood vessel. Since the stylet is also less likely to perforate the catheter, the possibility of fluid leakage from the catheter before the catheter reaches its final indwelling point also decreases.

Finally, unlike prior art catheter materials, the material used to form the present stylet does not expand substantially upon insertion and exposure to the patient's body temperature. Thus, because the stylet does not expand substantially when it softens, the stylet is easy to remove and the fluid flow area inside the catheter does not decrease. If the stylet expanded upon insertion in the patient's body, the fluid flow area would decrease in proportion to the increased size of the stylet. This causes manipulation and removal of the stylet to be more difficult, if not impossible, due to increased friction between the stylet and the catheter. All of this can result in greater patient discomfort and the possibility of the stylet perforating the catheter. In addition, the stylet and catheter assembly could possibly damage the blood vessel. These problems are avoided because the stylet of the present invention does not use the prior art softening and expandable material and thus, does not expand upon insertion in the patient.

One embodiment of the present invention is illustrated in FIGS. 1A–1E. FIGS. 1A–1E illustrate the placement of a long-line catheter, for example a PICC, into a blood vessel 101. A needle 109 is used to make the initial cut through the skin 100 as shown in FIG. 1A. Once the needle 109, the introducer 103 and its sheath 107 are in the patient's vessel 101, the needle 109 is removed and introducer 103 remains. The introducer 103 is comprised of a handle 105 coupled to a sheath 107.

Figure 1B:
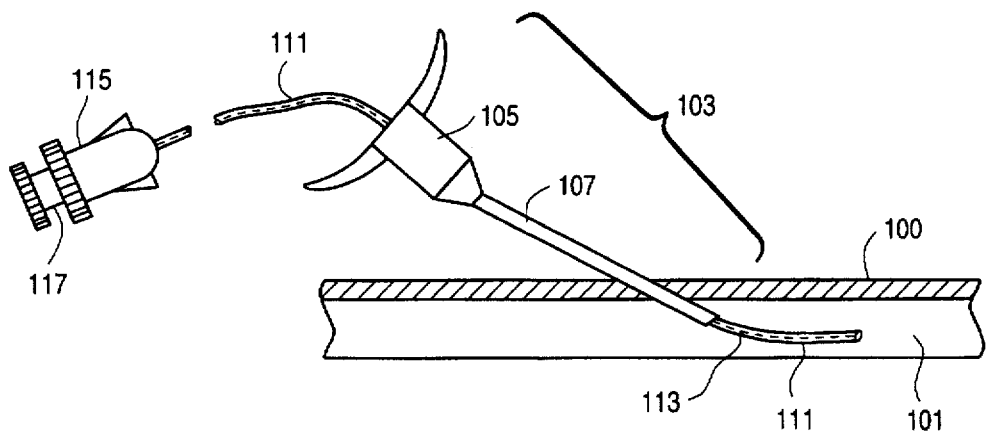

In FIG. 1B, a catheter 111 having a stylet 113 disposed within it is passed through the introducer 103 and into the patient's vessel 101. The catheter 111 and stylet 113 assembly are both gradually inserted and placed in patient's vessel 101. Stylet 113 remains stiff during the initial insertion, but softens quickly (e.g., a few seconds) at its distal end upon insertion of the distal end into the patient and exposure to the patient's body temperature. A break is shown in the catheter 111 to illustrate the fact that the entire length of the catheter 111 is not shown in FIG. 1B. The catheter 111 is attached at its proximal end to a catheter hub 115, which in turn is shown coupled to the stylet hub 117. It will be appreciated that a stylet hub may not always be present. The catheter hub 115 and the stylet hub 117 are used to help insert and place the catheter 111 and stylet 113 assembly in the patient's vessel 101.

Figure 1C:
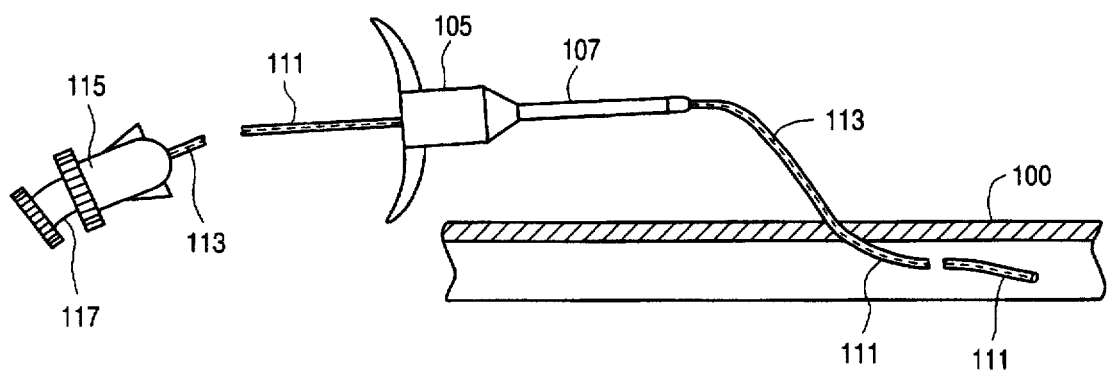
Figure 1D:
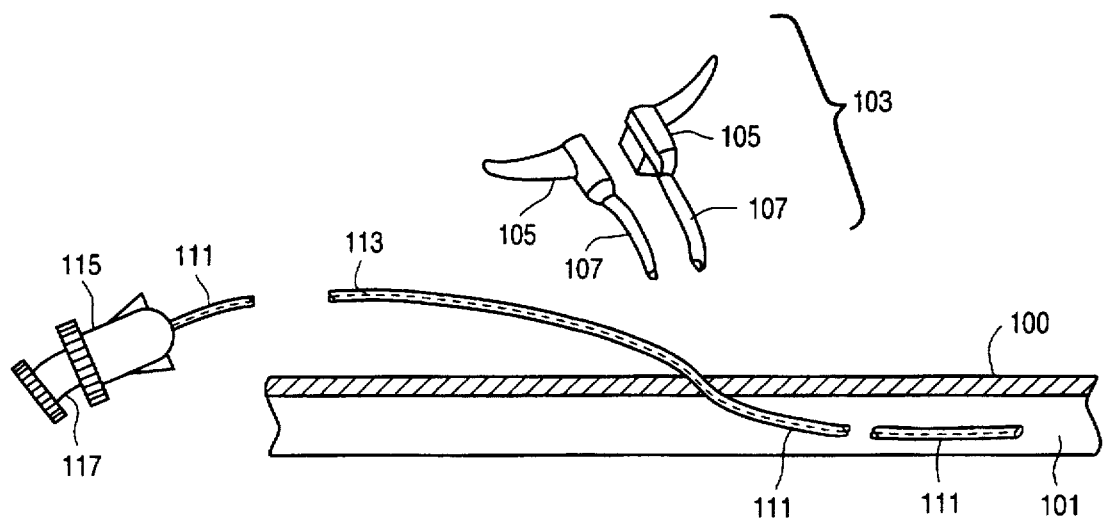
Figure 1E:
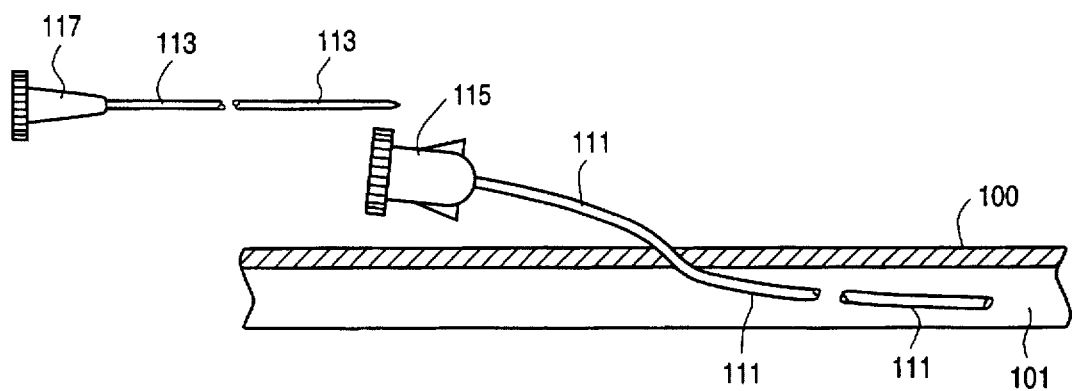

Once the catheter 111 is properly placed in the patient's vessel 101, the introducer 103 is removed from its location in the patient as shown in FIG. 1C. The sheath 107 is removed from the patient's vessel 101. The two breaks shown in catheter 111 illustrate the fact that the entire length of catheter 111 is not shown. In FIG. 1D, the introducer 103 is divided or peeled away and removed from the area. It is to be noted that the introducer 103 may also be peeled away from the catheter 111 while the introducer 103 is being removed. To facilitate the peeling away and removal of the introducer 103, the introducer handle 105 and sheath 107 may be made of a durable material of varying thickness. Once the catheter 111 and stylet 113 has reached its final indwelling point in the patient's vessel 101, the stylet is removed from the patient's vessel 101 and catheter 111 using the stylet hub 117. The catheter 111 is left in the patient's vessel 101. It will also be appreciated by one of skill in the art that the catheter 111 may be made of silicon, polyurethane, a thermally-softening material, a shape-memory material or any other bio-compatible material.

Although the stylet 113 is shown having a circular cross-section, it will be apparent that the stylet 113 may also have a variety of different configurations, for example, a substantially rectangular or elliptical cross-section. See, e.g., co-pending application, "A Stiffening Member To Increase Fluid Flow Within A Medical Device" that is also assigned to Johnson & Johnson Medical, Inc. Stylet 113 has a proximal end and a distal end. Upon insertion of the distal end of the stylet 113 within the catheter or outside of the catheter into the living subject, the stiffness of the distal end can decrease by at least 25 Durometer Shore D units or points. The stylet 113 softens almost instantaneously or within about a few seconds after it is exposed to the patient's body temperature. In most cases, the patient is a human with a body temperature of approximately 37° C.

The proximal end of the stylet (e.g., attached to stylet hub 117), and which is not inserted into the living subject, retains its current stiffness and does not soften. Because the proximal end remains stiff at room temperature, the attending physician or nurse is able to push against the proximal end of the stylet outside the patient to aid insertion through the introducer 103 and if present, its internal valve, which can cause the greatest resistance to catheter 111 and stylet 113 assembly insertion. In contrast, the distal end inside the patient is pliable and easily manipulated along the patient's blood vessel. This results in less potential vessel trauma and discomfort for the patient. In a preferred embodiment, the stylet can be made of a polyurethane-based shape memory polymer that is produced by Mitsubishi Heavy Industries, Ltd. and is available exclusively through Memry Technologies, Inc. located at 57 Commerce Drive, Brookfield, Conn. 06804.

Figure 2:
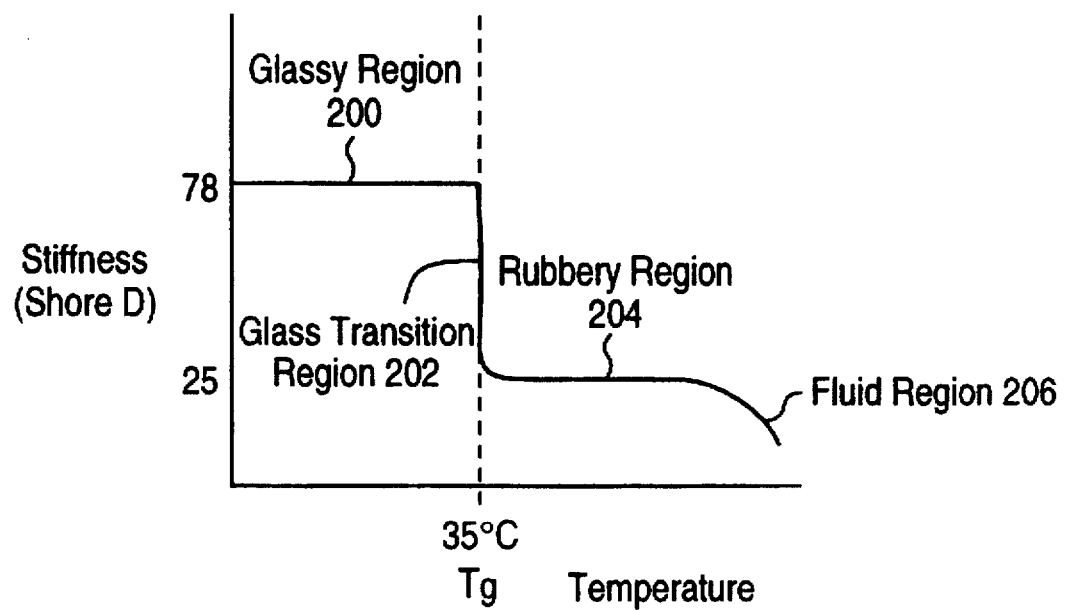
FIG. 2 is a graph showing how the material used in one embodiment changes at its glass transition temperature ($T_g$).

In a preferred embodiment, the stylet of the present invention can be made of a shape memory polymer known as MM-3510, which is available from Memry Technologies, Inc. located in Brookfield, Conn. Referring to FIG. 2, a graph illustrates how the hardness or stiffness of a stylet (made of MM-3510) changes in response to increasing temperatures, in particular at its glass transition temperature ($T_g$). MM-3510 is a shape memory polymer that is available in extrudable form and has a glass transition temperature of about 35° C. The glass transition point describes a unique property of glasses and polymers. Unlike metals, glasses and polymers do not crystallize on solidification. Instead, glasses and polymers, such as MM-3510, preserve the amorphous structure of a supercooled liquid in the glassy state 200. The glass transition point is the temperature at which the shape memory polymer or glass makes the transition 202 between a supercooled liquid and a glassy solid.

MM-3510 is in the glassy region 200 with a stiffness of 78 Shore D when it is exposed to a temperature below 35° C., its glass transition temperature ($T_g$). The glassy region 200 ranges between about 15° C. to 35° C. During its glass transition region 202, which occurs at approximately 35° C., the stiffness of material MM-3510 changes from about 78 Durometer Shore D to about 25 Durometer Shore D. Thus, at around 35° C., which is its $T_g$, MM-3510 becomes increasingly flexible and soft as it enters the glass transition region 202 and then rubbery region 204. The rubbery region 204 (for MM-3510) ranges between approximately 35° C. to 55° C. As the temperatures continue to increase beyond 55° C., it will enter into a fluid region 206.

Since the body temperature of most humans is about 37° C., shape memory polymer MM-3510 is perfect for use in forming a stylet or a catheter, which can be inserted into the human body. A stylet or catheter formed from shape memory polymer MM-3510 will dramatically soften within a few seconds upon insertion into a human body. It will be apparent to one of skill in the art that the stylet of the present invention may be made of other materials that have properties similar to shape memory polymer MM-3510. These properties include the temperature point (e.g. $T_g$) at which the material significantly softens.

It will also be appreciated that additional components, such as polyurethane, polyurethane-based polymers and various thermoplastics, may be added to shape memory polymer MM-3510 to achieve a greater stiffness in the stylet at certain points or throughout the entire stylet, or to achieve greater flexibility at other points during the insertion and placement of the stylet. It will also be apparent to one skilled in the art that the shape memory component of the present invention can be heated above its glass transition temperature and then formed into a desired shape, for example, a substantially rectangular stylet. See, e.g., co-pending application, "A Stiffening Member To Increase Fluid Flow Within A Medical Device" that is also assigned to Johnson & Johnson Medical, Inc. Thus, the use of the shape memory polymer MM-3510 to form the stylet of the present invention is meant to be illustrative and not limiting.

It will be apparent to one skilled in the art that a radiopacifier can be impregnated or added to shape memory polymer MM-3510 before extruding the stylet. The radiopacifier helps the stylet to be more visible on X-ray. Some exemplary radiopacifiers are barium sulfate, bismuth subcarbonate, bismuth trioxide, tungsten and tantalum.

It will be noted the present invention may be used in a medical device, other than a catheter. For example, the present invention can be used with a stent, or any other device that would normally require a guidewire or a stylet or a scope.

The foregoing description provides an example of a stiffening member, such as a stylet, disposed within a medical device, such as a PICC. It will be appreciated that numerous modifications may be made in practicing the present invention without departing from the spirit and scope of the invention, which is defined by the following claims.

We claim:

1. A catheter stylet having a proximal end and a distal end, comprising:

an elongated member having a substantially uniform cross-section and a cross-sectional area, wherein upon insertion of the distal end into a living body, the distal end of the stylet softens by at least a factor of three in response to a body temperature of the living body and substantially maintains the cross-sectional area.

2. The stylet of claim 1, wherein upon insertion of the distal end into the living body, the distal end of the stylet softens by at least 50 Durometer Shore D units.

3. The stylet of claim 1, wherein the distal end softens in a few seconds after being inserted into the living body.

4. The stylet of claim 1, wherein the elongated member has a glass transition temperature of approximately 35° C.

5. The stylet of claim 1, wherein a component has been added to the elongated member to modify the stiffness throughout the elongated member.

6. The stylet of claim 1, wherein a component has been added to the elongated member to modify the stiffness at least at one point in the elongated member.

7. A vascular access device, comprising:

a catheter having a lumen; and a stylet having a cross-sectional area and a physical property such that the stylet is capable of softening by at least a factor of three and substantially maintaining the cross-sectional area when exposed to a predetermined temperature, wherein the stylet is disposed within the lumen of the catheter.

8. The vascular access device of claim 7, wherein the catheter also softens when exposed to the predetermined temperature by at least 50 Durometer Shore D units.

9. The vascular access device of claim 7, wherein the predetermined temperature is about 35° C.

10. The vascular access device of claim 7, wherein the stylet comprises a distal end and a proximal end and wherein upon insertion of the distal end into a living subject, the distal end softens.

11. The vascular access device of claim 10, wherein the distal end of the stylet softens in a few seconds when inserted into the living subject.

12. The vascular access device of claim 10, wherein the distal end of the stylet softens so that its stiffness decreases at least 50 Durometer Shore D units.

13. The vascular access device of claim 8, wherein the stylet has a distal end and a proximal end, and wherein upon insertion of the distal end into a living body and exposure to the predetermined temperature of approximately 35° C., the distal end of the stylet softens.

14. The vascular access device of claim 7, wherein a radiopacifier has been added to the stylet.

15. The vascular access device of claim 14, wherein the radiopacifier is selected from a group consisting of barium sulfate, bismuth subcarbonate, bismuth trioxide, tungsten and tantalum.

16. A stent stylet comprising:

an elongated member having a proximal end and a distal end and a substantially uniform cross-section, the distal end of the stylet having a physical property such that upon insertion into a living body, the distal end of the stylet softens by at least a factor of three in response to a body temperature of the living body.

17. The stent stylet of claim 16, wherein upon insertion of the distal end into the living body, the distal end of the stylet softens by at least 50 Durometer Shore D units.

* * * * *